(12) United States Patent
Borisy et al.

(10) Patent No.: US 6,846,816 B2
(45) Date of Patent: *Jan. 25, 2005

(54) COMBINATIONS OF DRUGS FOR THE TREATMENT OF NEOPLASTIC DISORDERS

(75) Inventors: Alexis Borisy, Boston, MA (US); Curtis Keith, Boston, MA (US); Michael A. Foley, Chestnut Hill, MA (US); Brent R. Stockwell, Boston, MA (US)

(73) Assignee: CombinatoRx, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/347,714

(22) Filed: Jan. 21, 2003

(65) Prior Publication Data

US 2003/0166642 A1 Sep. 4, 2003

Related U.S. Application Data

(63) Continuation of application No. 09/706,929, filed on Nov. 6, 2000, now Pat. No. 6,569,853.

(51) Int. Cl.[7] .............................................. A61K 31/54
(52) U.S. Cl. ................................ 514/225.8; 514/224.8; 514/225.2; 514/225.5; 514/226.2
(58) Field of Search ........................... 514/225.8, 224.8, 514/225.2, 225.5, 226.2

(56) References Cited

U.S. PATENT DOCUMENTS

| | | | |
|---|---|---|---|
| 5,104,858 A | 4/1992 | Hait et al. | |
| 5,770,585 A | 6/1998 | Kaufman et al. | |
| 6,569,853 B1 * | 5/2003 | Borisy et al. ............ | 514/226.2 |

FOREIGN PATENT DOCUMENTS

| | | | |
|---|---|---|---|
| GB | 1288376 | 9/1972 | |
| WO | WO 01/35935 | 5/2001 | ............ 31/155 |

OTHER PUBLICATIONS

Akiyama et al., "Circumvention of Multiple–Drug Resistance in Human Cancer Cells by Thioridazine, Trifluoperazine, and Chlorpromazine," *J. Natl. Cancer Inst.* 76:839–844 (1986).
Al–Abdely et al., "Efficacies of KY62 Against *Leishmania amazonensis* and *Leishmania donovani* in Experimental Murine Cutaneous Leishmaniasis and Visceral Leishmaniasis," *Antimicrob. Agents Chemother.* 42:2542–2548 (1998).
Andres et al., "Biochemical Effects of Chlorpromazine on Mouse Neuroblastoma Cells," *Vet. Hum. Toxicol.* 41:273–278 (1999).
Anees et al., "Inhibition of a Tumor Protease with 3,4–Dichloroisocoumarin, Pentamidine–Isethionate and Guanidino Derivatives," *J. Enzyme Inhibition* 8:213–221 (1994).
Bailly et al., "Sequence–Specific DNA Minor Groove Binders. Design and Synthesis of Netropsin and Distamycin Analogues," *Bioconjug. Chem.* 9:513–538 (1998).
Bailly et al., "Sequence–Selective Binding to DNA of bis(amidinophenoxy) Alkanes Related to Propamidine and Pentamidine," *Biochem. J.* 323:23–31 (1997).
Barak et al., "The Effect of Chlorpromazine and Haloperidol on DNA Transcription," *Int. Clin. Psychopharmacol.* 11:193–197 (1996).
Barancik et al., "Reversal effects of Several Ca2+ Entry Blockers, Neuroleptics and Local Anesthetics on P–Glycoprotein Mediated Vincristine Resistance of L 1210/VCR Mouse Leukaemic Cell Line," *Drugs Exptl. Clin. Res.* 20:13–18 (1994).
Barrett et al., "Anti–Sleeping Sickness Drugs and Cancer Chemotherapy," *Parasitology Today* 16:7–9 (2000).
Bebawy et al., "Selective Modulation of P–Glycoprotein–Mediated Drug Resistance," *Brit J. Cancer* 85:1998–2003 (2001).
Beckett et al., "Metabolism of Chlorpromazine and Promazine in vitro: Isolation and Characterization of N–Oxidation Products," *Xenobiotica* 18:61–74 (1988).
Bell et al., "Structure–Activity Relationships of Pentamidine Analogs Against *Giardia lamblia* and Correlation of Antigiardial Activity with DNA–Binding Affinity," *Antimicrob. Agents Chemother.* 35:1099–1107 (1991).
Benaim et al., "A Calmodulin–Stimulated Ca 2+ Pump in Plasma–Membrane Vesicles from *Trypanosoma brucei*; Selective Inhibition by Pentamidine," *Biochem J* 296:759–63 (1993).
Bleeker et al., "The Effects of Dexamethazone and Chlorpromazine on Tumor Necrosis Factor–Alpha, lnterleukin–1 Beta, lnterleukin–1 Receptor Antagonist and Interleukin–10 in Human Volunteers," *Immunology* 91:548–552 (1997).
Bornstein et al., "An Evalution of the Mechanism of Action of Pentamidine Isethionate," *Journal of Surgical Oncology* 2:393–398 (1970).
Borsa et al., "Selective Cytotoxicity of Calmidazolium and Trifluoperazine For Cycling Verses Noncycling C3H10T1/2 cells In Vitro," *Cancer Res.* 46:133–136 (1986).
Chen et al., "Anti–Tumor Necrosis Factor Properties of Non–Peptide Drugs in Acute–Phase Responses," *Eur. J. Pharmacol.* 271:319–327 (1994).
Clancy et al., "Chlorpromazine Modulates Cytokine Expression in the Liver and Lung After Burn Injury and Endotoxemia," *J. Trauma* 48:215–222 (2000).
Corsini et al., "Induction of Tumor Necrosis Factor–Alpha In Vivo by a Skin Irritant, Tributytin, Through Activation of Transcription Factors: Its Pharmacological Modulation by Anti–Inflammatory Drugs," *J. Invest. Dermatol.* 108: 892–896 (1997).

(List continued on next page.)

Primary Examiner—Peter G O'Sullivan
(74) Attorney, Agent, or Firm—Clark & Elbing LLP

(57) ABSTRACT

The invention features a method for treating a patient having a cancer or other neoplasm by administering to the patient two compounds simultaneously or within 14 days of each other in amounts sufficient to treat the patient.

13 Claims, No Drawings

OTHER PUBLICATIONS

Cresson et al., "In Vitro Inhibition of Human Sarcoma Cells' Invasive Ability by Bis(5–Amidino–2–Benzimidazolyl) Methane–a novel esteroprotease inhibitor," *Am. J. Pathol.* 123:46–56 (1986).

Cubria et al., "Aromatic Diamidines are Reversible Inhibitors of Porcine Kidney Diamine Oxidase," *Biochem. Pharmacol.* 45:1355–1357 (1993).

Darkin et al., "Chlorpromazine: A Potential Anticancer Agent?," *Biochem. Biophys. Res. Commun.* 125:184–191 (1984).

Dautzenberg et al., "Pentamidine Aerosol in the Preventive Treatment of Pneumocystosis in AIDS Patients. Comparison of Two Salts and Two Nebulizers," *Presse. Med.* 20:1117–1120 (1991).

Del Poeta et al., "Structure–In Vitro Activity Relationships of Pentamidine Analogues and Dication–Substituted Bis–Benzimidazoles as New Antifungal Agents," *Antimicrob. Agents Chemother.* 42:2495–2502 (1998).

Driscoll et al., "Pyschotropic Drugs as Potential Antitumor Agents: A Selective Screening Study," *Cancer Treatment Rep.* 62:45–74 (1978).

Ferroni et al., "N1–Substituted Benzamidines: Synthesis, Antiproteinase Activity and Inhibition of Tumor Cell Growth," *II Farmaco* 46:1311–1321 (1991).

Fibach et al., "Phorbol Ester–Induced Adhesion of Murine Erythroleukemia Cells: Possible Involvement of Cellular Proteases," *Carcinogenesis*, 4:1395–1399, 1983.

Fimognari et al., "Flow Cytometric Analysis of Genetic Damage, Effect on Cell Cycle Progression, and Apoptosis by Thiophanate–Methyl in Human Lymphocytes," *Environ. Mol. Mutagen.* 33:173–176 (1999).

Ferroni et al., "N1–Substituted Benzamidines: Synthesis, Antiproteinase Activity and Inhibition of Tumor Cell Growth," *Farmaco* 46:1311–1321 (1991).

Ford et al., "Structural Features Determining Activity of Phenothiazines and Related Drugs for Inhibition of Cell Growth and Reversal of Multidrug Resistance," *Molecular Pharmacology* 35:105–115 (1989).

Fraser et al., "Endo–Exonuclease of Human Leukaemic Cells: Evidence for a Role in Apoptosis," *J. Cell Sci.* 109:2343–2360 (1996).

Gambari et al., "DNA–Binding Activity and Biological effects of Aromatic Polyamidines," *Biochem Pharmacol* 47:599–610 (1994).

Ganapathi et al., "Factors Governing the Modulation of Vinca–Alkaloid Resistance in Doxorubicin–Resistant Cells by the Calmodulin InhibItor Trifluoperazine," *Biochemical Pharmacology* 35:673–678 (1986).

Hait et al., "Antitumor and Toxic Effects of Combination Chemotherapy with Bleomycin and a Phenothiazine Anticalmodulin Agent," *J. Natl. Cancer Inst.* 80:246–250 (1988).

Herberich et al., "Synthesis of a Netropsin Conjugate of a Water–Soluble epi–Quinocarcin Analogue: the Importance of Stereochemistry at Nitrogen," *Bioorganic & Medicinal Chemistry* 8:523–532 (2000).

Huilgol et al., "Assessment of Chlorpromazine as Radiation Sensitizer and Protector," *Indian Journal of Cancer* 31:195–200 (1996).

Huilgol et al., "A clinical Study to Assess Chlorpromazine as Hypoxic Cell Sensitizer in Head and Neck Cancer Treated with Conventional Radiation," *Indian Joumal of Cancer* 35:97–100 (1998).

Ishikawa et al., "Exacerbation of Doxorubicin Lethality by Chlorpromazine in Mice," *Jpn. J. Pharmacol.* 55:291 (1991).

Ishikawa et al., "Protection Against Cisplatin and Doxorubicin Toxicity in BALB/C Mice by Chlorpromazine Hypothermia," *Research Communications in Psychology, Psychiatry, and Behavior* 16:93–96 (1991).

Jansen et al, "Chlorpromazine Down–Regulates Tumor Necrosis Factor–Alpha and Attenuates Experimental Multiple Organ Dysfunction Syndrome in Mice," *Crit. Care Med.* 26:1244–1250 (1998).

Jiang et al., "Transformation of Lupus–Inducing Drugs to Cytotoxic Products by Activated Neutrophils," *Science* 266:810–813 (1994).

Jones, "Successful Cancer Therapy with Promethazine: The Rationale," *Med. Hypotheses* 46:25–29 (1996).

Kim et al., "Effects of Calmodulin Antagonists and Anesthetics on the Skin Lesions Induced by 2–Chloroethylethyl Sulfide," *Eur. J. Pharmacol.* 313:107–114 (1996).

Kitamura et al., "Inhibition of Constitutive Nitric Oxide Synthase in the Brain by Pentamidine, a Calmodulin Antagonist," *Eur. J. Pharmacol.* 289:299–304 (1995).

Klemes et al., "Inhibition of Phorbol–Ester–Induced Adhesion of Differentiating Human Myeloid Leukemic Cells by pentamidine–Isethionate," *Differentiation* 27:141–145 (1984).

Kopac, M.J., "Section of Biology," *The New York Academy of Sciences* 5–10 (1945).

Kopac, M.J., "Some Cellular and Surface Chemical Aspects of Tumor Chemotherapy," in *Approaches to Tumor Chemotherapy* ed. F.R. Moulton, AAAS, Washington, D.C. (1947).

Krishan et al., "Synergistic Effects of Prochlorperazine and Dipyridamole on the Cellular Retention and Cytotoxicity of Doxorubicin," *Clinical Cancer Research* 6:1508–1517 (2000).

Kumar et al., "Inhibition of Protein Synthesis by Antagonists of Calmodulin in Ehrlich Ascites Tumor Cells," *Eur. J. Biochem.* 195:313–319 (1991).

Libby et al., "Inhibition of Enzymes of Polyamine Back–Conversion by Pentamidine and Berenil," *Biochemical Parmacology* 44:830–832 (1992).

Luck et al., "Interaction of Nonintercalative Antitumour Drugs SN–6999 and SN–18071 with DNA: Influence of Ligand Structure on the Binding Specificity," *Journal of Biomolecular Structure & Dynamics* 4:1079–1094 (1987).

Mesa–Valle et al., "In Vitro Action of Platinum (II) and Platinum (IV) Complexes on *Trypanosoma cruzi* and *Leishmania donovani*," *Azneimittelforschung* 39:838–842 (1989).

Mesa–Valle et al., "In Vitro and In Vivo Activity of Two Pt(IV) Salts Against *Leishmania donovani*," *Pharmacology* 57:160–72 (1998).

Mesa–Valle CM et al., "Action of New Organornetallic Complexes Against *Leishmania donovani*," *J. Antimicrob. Chemother.* 40:47–57 (1997).

Miller et al., "Clinical Modulation of Doxorubicin Resistance by the Calmodulin Inhibitor, Trifluoperazine: A Phase I/Il Trial," *Journal of Clinical Oncology*, 6:880–888 (1988).

Mongiardo et al., "Pentamidine Salts," *Lancet* 2:108 (1989).

Naito et al., "Competitive Inhibition by Verapamil of ATP–Dependent High Affinity Vincristine Binding to the Plasma Membrane of Mutidrug Resistant K562 Cells Without Calcium Ion Involvement," *Cancer Research* 49:1452–1455 (1989).

Nastruzzi et al., "Inhibition of 'In Vitro' Tumor Cell Growth by Aromatic Polyamidines Exhibiting Antiproteinase Activity," *Clin. ExpI. Metastasis* 7:25–39 (1989).

Nastruzzi et al., "Differential Effects of Benzamidine Derivatives on the Expression of C–MYC and HLA–DRα Genes in a Human B–Lymphoid Tumor Cell Line," *Cancer Letters* 38:297–305 (1988).

Navas et al., "Structural Determinants of Putrescine Uptake Inhibition Produced by Cationic Diamidines in the Model of Trypanosomatid Crithidia Fasciculata," *Biol. Chem.* 377:833–836 (1996).

Nishimura et al., "A Serine Protease–Inhibitory Benzamidine Derivative Inhibits the Growth of Human Colon Carcinoma Cells," *Jpn. J. Cancer Res.* 83:723–728 (1992).

Nordenberg et al., "Effects of Psychotropic Drugs on Cell Proliferation and Differentiation," *Biochemical Pharmacology* 58:1229–1236 (1999).

Nunn et al., "Sequence–Dependent Drug Binding to the Minor Groove of DNA: Crystal Structure of the DNA Dodecamer d(CGCAAATTTGCG)$_2$ Complexed with Propamidine," *J. Med. Chem.* 38:2317–2325 (1995).

Ohtsuka et al., "Inhibitory Effect on LPS–lnduced Tumor Necrosis Factor in Calves Treated with Chlorpromazine or Pentoxifylline," *J. Vet. Med. Sci.* 59:1075–1077 (1997).

Osei et al., "Diabetogenic Effect of Pentamidine," *Am. J. Med.* 77:41–46 (1984).

Palmer et al., "Correlation of Activity of Chlorpromazine and Respective Hydroxy, Dimethoxy and Sulphoxide Analogues on Dopamine. Muscarinic, Histamine and Calmodulin Sites of Action," *Xenobiotica* 18:277–289 (1988).

Perez et al., "DNA Binding Properties and Antileukemic (L1210) Activity of Pt–Pentamidine Complex," *Chem. Biol. Interact* 77:341–55 (1991).

Perez et al., "Binding of Pt–Pentamidine to Nucleosomal DNA. Studies of the Antiproliferative Activity of the Drug Against Human Cancer Cells," *Chemico–Biological Interactions* 89:61–72 (1993).

Prokopenko et al., "Effects of Haloperidol and Chlorpromazine on Smooth Muscle Contractility, Platelet Aggregation an Neuronal Calcium Current," *Gen. Physiol. Biophys.* 14:349–357 (1995).

Reddy et al., "Synthetic DNA Minor Groove–Binding Drugs," *Pharmacology & Therapeutics* 84:1–111 (1999).

Rosenthal et al., "Pentamidine: An inhibitor of Interleukin–1 that Acts Via a Post–Translational Event," *Toxicol. Appl. Pharmacol.* 107:555–561 (1991).

Sands et al., "Pentamidine: A Review," *Reviews of Infectious Diseases*, 7:625–634, 1985.

Sansom et al., "Structural Studies on Bio–Active Compounds. Part XIV. Molecular Modelling of the Interactions Between Pentamidine and DNA," *Anti–Cancer Drug Design*, 5:243–245, 1990.

Schoenbach et al., "The Pharmacology, Mode of Action and Therapeutic Potentialities of Stilbamidine, Pentamidine, Propamidine and Other Aromatic Diamidines–A Review," *Medicine*, 27:327–377, 1948.

Snapper, I., "Stilbamidine and Pentamidine in Multiple Myeloma," *J.A.M.A.* 133:157–161. (1947).

Snapper, I., "On the Influence of Stilbamidine Upon Multiple Myeloma," *Journal of the Mount Sinai Hospital* 8:119–127 (1946).

Smid et al., "Radiotherapy, Combined with Simultaneous Chemotherapy with Mitomycin C and Bleomycin for Inoperable Head and Neck Cancer–Preliminary Report," *Int. J. Radiat. Oncol. Biol. Phys.* 32:769–75 (1995).

Syed et al., "Reversal of Vinblastine Transport by Chlorpromazine in Membrane Vesicles from Multidrug–Resistant Human CCRF–CEM Leukaemia Cells," *British Journal Of Cancer* 78:321–327 (1998).

Tidwell et al., "Analogues of 1,5–Bis(4–amidinophenoxy) pentane (Pentamidine) in the Treatment of Experimental Pneumocystis carinii Pneumonia," *J. Med. Chem.* 33:1252–1257 (1990).

Tsuruo et al., "Overcoming of Vincristine Resistance in P388 Leukemia in Vivo and In Vitro through Enhanced Cytotoxicity of Vincristine and Vinblastine by Verapamil," *Cancer Research* 41:1967–1972 (1981).

Tsuruo et al., "Increased Accumulation of Vincristine and Adriamycin in Drug Resistant P388 Tumor Cells Following IncubatIon with Calcium Antagonist and Calmodulin Inhibitors," *Cancer Research* 42:4730–4733 (1982).

Tsuruo et al., "Potentiation of Antitumor Agents by Calcium Channel Blockers with Special Reference to Cross Resistance Patterns," *Cancer Chemotherapy and Pharmacology* 15:16–19 (1985).

Turner et al., "The Mutagenic Properties of DNA Minor–Groove Binding Ligands," *Mutation Research* 355:141–169 (1996).

Ueda et al., "Chlorpromazine Reduces Toxicity and Ca2+ Uptake Induced by Amyloid Beta Protein (25–35) In Vitro," *Brain Res* 748:184–8 (1997).

Van Wauwe et al., "The Inhibitory Effect of Pentamidine on the Production of Chemotactic Cytokines by In Vitro Stimulated Human Blood Cells," *lnflamrn. Res.* 45:357–63 (1996).

Waalkes et al., "Pentamidine" Clinical Pharmacologic Correlations in Man and Mice, *Clinical Pharmacology & Therapeutics* 11:505–512 (1970).

Wils et al., "Polarized Transport of Docetaxel and Vinblastine Mediated by P–Glycoprotein in Human Intestinal Epithelial Cell Monolayers," *Biochemical Pharmacology* 48:1528–1530 (1994).

Zakotnik et al., "Concomitant Radiotherapy with Mitomycin C and Bleomycin Compared with Radiotherapy Alone in Inoperable Head and Neck Cancer: Final Report," *Int. J. Radiation Oncology Biol. Phys.* 41:1121–1127 (1998).

Zakrzewska et al., "The Solvation Contribution to the Binding Energy of DNA with Non–Intercalating Antibiotics," *Nucleic Acids Res.* 12:6559–74 (1984).

National Cancer Institute Developmental Therapeutics Program In–Vitro Testing Results, NSC 620107 Experiment ID 9407SR53–57, 1994.

* cited by examiner

COMBINATIONS OF DRUGS FOR THE TREATMENT OF NEOPLASTIC DISORDERS

CROSS-REFERENCE TO RELATED APPLICATIONS

This application is a continuation of U.S. application Ser. No. 09/706,929, filed Nov. 6, 2000 now U.S. Pat. No. 6,569,853.

BACKGROUND OF THE INVENTION

The invention relates to the treatment of neoplastic disorders such as cancer.

Cancer is a disease marked by the uncontrolled growth of abnormal cells. The abnormal cells may no longer do the work of normal cells, and they crowd out and destroy healthy tissue.

Lung cancer is the most common cancer-related cause of death among men and women. It is the second most commonly occurring cancer among men and women; it has been estimated that there will be more than 164,000 new cases of lung cancer in the U.S. in the year 2000 alone. While the rate of lung cancer cases is declining among men in the U.S., it continues to increase among women. Lung cancer can be lethal; according to the American Lung Association, an estimated 156,900 Americans are expected to die due to lung cancer in 2000.

Cancers that begin in the lungs are divided into two major types, non-small cell lung cancer and small cell lung cancer, depending on how the cells appear under a microscope. Non-small cell lung cancer (squamous cell carcinoma, adenocarcinoma, and large cell carcinoma) generally spreads to other organs more slowly than does small cell lung cancer. Small cell lung cancer is the less common type, accounting for about 20% of all lung cancer.

Other cancers include brain cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, and uterine cancer. These cancers, like lung cancer, are sometimes treated with chemotherapy.

Chemotherapeutic drugs currently in use or in clinical trials include paclitaxel, docetaxel, tamoxifen, vinorelbine, gemcitabine, cisplatin, etoposide, topotecan, irinotecan, anastrozole, rituximab, trastuzumab, fludarabine, cyclophosphamide, gentuzumab, carboplatin, interferon, and doxorubicin. The most commonly used anticancer agent is paclitaxel, which is used alone or in combination with other chemotherapy drugs such as: 5-FU, doxorubicin, vinorelbine, cytoxan, and cisplatin.

SUMMARY OF THE INVENTION

We have discovered that the combination of the antipsychotic drug chlorpromazine and the antiprotozoal drug pentamidine exhibits substantial antiproliferative activity against cancer cells. Structural and functional analogs of each of these compounds are known, and any of these analogs can be used in the antiproliferative combination of the invention. Metabolites of chlorpromazine and pentamidine are also known. Many of these metabolites share one or more biological activities with the parent compound and, accordingly, can also be used in the antiproliferative combination of the invention. Accordingly, the invention features a method for treating a patient having a cancer or other neoplasm, by administering to the patient chlorpromazine and pentamidine simultaneously or within 14 days of each other in amounts sufficient to inhibit the growth of the neoplasm.

Preferably, the two compounds are administered within ten days of each other, more preferably within five days of each other, and most preferably within twenty-four hours of each other or even simultaneously. The cancer treated according to any of the methods of the invention, described below, can be lung cancer (squamous cell carcinoma, adenocarcinoma, or large cell carcinoma), brain cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, or uterine cancer.

In a related aspect, the invention also features a method for treating a patient having a neoplasm such as cancer. In this method, the patient is administered (a) a first compound selected from prochlorperazine, perphenazine, mepazine, methotrimeprazine, acepromazine, thiopropazate, perazine, propiomazine, putaperazine, thiethylperazine, methopromazine, chlorfenethazine, cyamemazine, perphenazine, enanthate, norchlorpromazine, trifluoperazine, thioridazine (or a salt of any of the above), and dopamine D2 antagonists (e.g., sulpride, pimozide, spiperone, ethopropazine, clebopride, bupropion, and haloperidol); and (b) a second compound selected from propamidine, butamidine, heptamidine, nonamidine, stilbamidine, hydroxystilbamidine, diminazene, benzamidine, 4,4'-(pentamethylenedioxy) di-, dihydrochloride, phenamidine, dibrompropamidine, 1,3-bis (4-amidino-2-methoxyphenoxy)propane, phenamidine, and amicarbalide (or a salt of any of the above). Alternatively, the second compound can be a functional analog of pentamidine, such as netropsin, distamycin, bleomycin, actinomycin, or daunorubicin. The first and second compounds are preferably administered simultaneously or within 14 days of each other and in amounts sufficient to inhibit the growth of the neoplasm.

In another related aspect, the invention also features a method for treating a patient having a neoplasm such as cancer by administering the following:

a) a first compound having the formula (I):

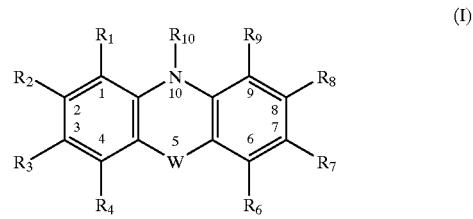

(I)

wherein $R_2$ is selected from the group consisting of:

----$CF_3$     A-1

----$Cl$     A-2

----$F$     A-3

----$OCH_3$     A-4

----$\stackrel{CH_3}{\underset{O}{\diagdown}}$     A-5

----≡N     A-6

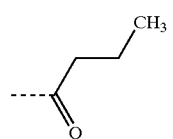 A-7
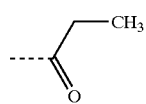 A-8
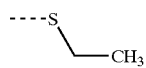 A-9
 A-10
$R_{10}$ is selected from the group consisting of:
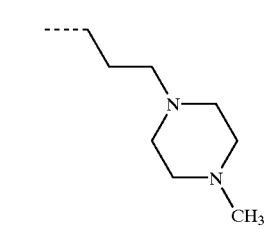 B-1
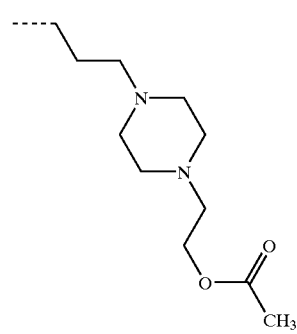 B-2
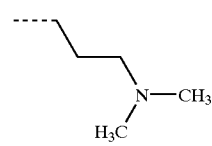 B-3
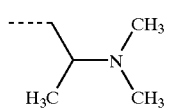 B-4
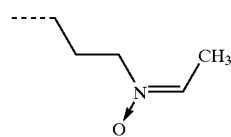 B-5
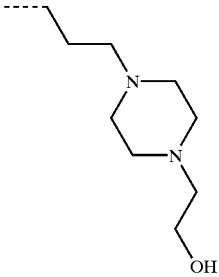 B-6
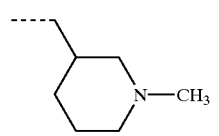 B-7
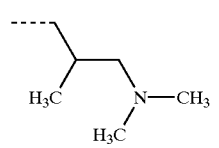 B-8, B-9, B-10, B-11, B-12, B-13, B-14, B-15, B-16
each of $R_1$, $R_3$, $R_4$, $R_5$, $R_6$, $R_7$, $R_8$, and $R_9$ is, independently, H, F, OH, $OCF_3$, or $OCH_3$; and W is selected from the group consisting of:

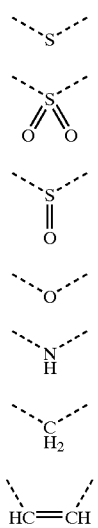

C-1
C-2
C-3
C-4
C-5
C-6
C-7 and
b) a second compound having the formula (II):

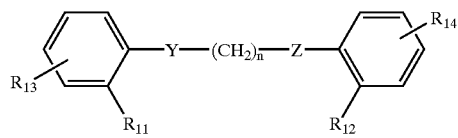

(II)

wherein each of Y and Z is, independently, O or N; each of $R_{11}$ and $R_{12}$ is, independently, H, OH, Cl, Br, $OCH_3$, $OCF_3$, $NO_2$, or $NH_2$; n is an integer between 2 and 6, inclusive; and each of $R_{13}$ and $R_{14}$ is, independently, at the meta or para position and is selected from the group consisting of:

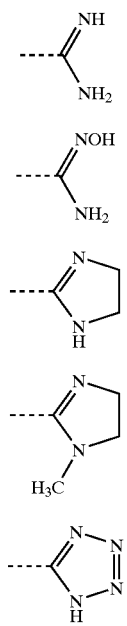

D-1
D-2
D-3
D-4
D-5 wherein the first and second compounds are administered simultaneously or within 14 days of each other in amounts sufficient to inhibit the growth of the neoplasm.

In any of the foregoing treatments, each compound that is part of the combination is preferably administered to the patient as part of a pharmaceutical composition that also includes a pharmaceutically acceptable carrier. Chlorpromazine is preferably administered at a dosage of 10 to 2500 milligrams and pentamidine is preferably administered at a dosage of 1 to 1000 milligrams. Preferred modes of administration include intravenous, intramuscular, inhalation, and oral administration.

The antiproliferative combinations of the invention can be part of a pharmaceutical pack. Preferably, the chlorpromazine and pentamidine are formulated together or separately and in individual dosage amounts.

It will be understood by those in the art that the compounds are also useful when formulated as salts. For example, as is described herein, the isethionate salt of pentamidine exhibits synergistic antiproliferative activity when combined with chlorpromazine. Other salts of pentamidine include the platinum salt, the dihydrochloride salt, and the dimethanesulfonate salt (see, for example, Mongiardo et al., Lancet 2:108, 1989). Similarly, chlorpromazine salts include, for example, hydrochloride salts and maleate salts.

The invention also features methods for identifying compounds useful for treating a patient having a neoplasm. The method includes the steps of contacting cancers cell in vitro with (i) pentamidine or chlorpromazine and (ii) a candidate compound, and determining whether the cancer cells grow more slowly than (a) cancer cells contacted with the chlorpromazine or pentamidine but not contacted with the candidate compound, and (b) cancer cells contacted with the candidate compound but not with chlorpromazine or pentamidine. A candidate compound that, when combined with chlorpromazine or pentamidine, reduces cell proliferation but, in the absence of chlorpromazine or pentamidine, does not is a compound that is useful for treating a patient having a neoplasm.

Combination therapy may be provided wherever chemotherapy is performed: at home, the doctor's office, a clinic, a hospital's outpatient department, or a hospital. Treatment generally begins at a hospital so that the doctor can observe the therapy's effects closely and make any adjustments that are needed. The duration of the combination therapy depends on the kind of cancer being treated, the age and condition of the patient, the stage and type of the patient's disease, and how the patient's body responds to the treatment. Drug administration may be performed at different intervals (e.g., daily, weekly, or monthly) and the administration of each agent can be determined individually. Combination therapy may be given in on-and-off cycles that include rest periods so that the patient's body has a chance to build healthy new cells and regain its strength.

Depending on the type of cancer and its stage of development, the combination therapy can be used to treat cancer, to slow the spreading of the cancer, to slow the cancer's growth, to kill or arrest cancer cells that may have spread to other parts of the body from the original tumor, to relieve symptoms caused by the cancer, or to prevent cancer in the first place. Combination therapy can also help people live more comfortably by eliminating cancer cells that cause pain or discomfort.

Other features and advantages of the invention will be apparent from the following detailed description, and from the claims.

DETAILED DESCRIPTION OF THE INVENTION

We have discovered that the combination of the antipsychotic drug chlorpromazine and the antiprotozoal drug pentamidine exhibits substantial antiproliferative activity against cancer cells. Concentrations that exhibited maximal antiproliferative activity against cancer cells were not toxic to normal cells. Thus, this drug combination is useful for the treatment of cancer and other neoplasms.

Based on known properties that are shared between chlorpromazine and its analogs and metabolites, and between pentamidine and its analogs and metabolites, it is likely that structurally related compounds can be substituted for chlorpromazine and/or pentamidine in the antiproliferative combinations of the invention. Information regarding each of the drugs and its analogs and metabolites is provided below.

Phenothiazines

Phenothiazines that are useful in the antiproliferative combination of the invention are compounds having the general formula (I):

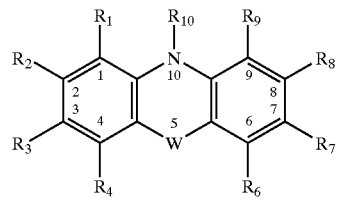
(I)

wherein $R_2$ is selected from the group consisting of:

----$CF_3$  A-1

----$Cl$  A-2

----$F$  A-3

----$OCH_3$  A-4

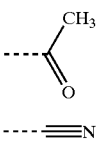  A-5

----≡N  A-6

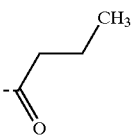  A-7

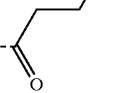  A-8

----S—$CH_3$  A-9

(with branch CH_3)

----$OCF_3$  A-10 each of $R_1$, $R_3$, $R_4$, $R_5$, $R_6$, $R_7$, $R_8$, and $R_9$ is, independently, H, OH, F, $OCF_3$, or $OCH_3$; W is selected from the group consisting of:

  C-1

-continued

  C-2

  C-3

  C-4

  C-5

  C-6

  C-7 and $R_{10}$ is selected from the group consisting of:

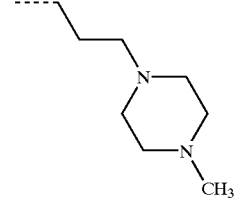  B-1

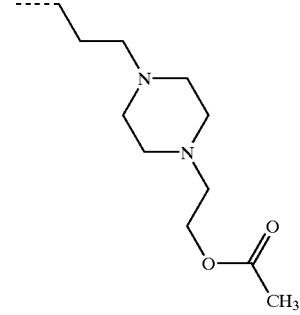  B-2

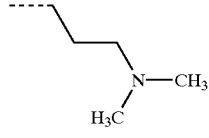  B-3

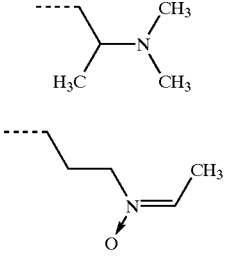  B-4

B-5

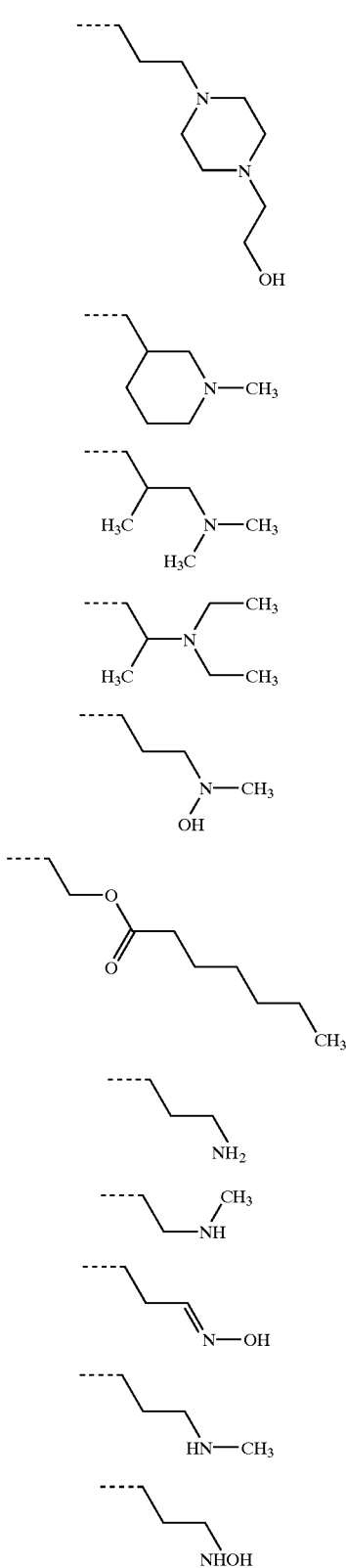

B-6
B-7
B-8
B-9
B-10
B-11
B-12
B-13
B-14
B-15
B-16

In preferred compounds, $R_2$ is Cl; each of $R_1$, $R_3$, $R_4$, $R_5$, $R_6$, $R_7$, $R_8$, and $R_9$ is H or F. More preferably, each of $R_1$, $R_4$, $R_5$, $R_6$, and $R_9$ is H.

The most commonly prescribed member of the phenothiazine family is chlorpromazine, which has the structure:

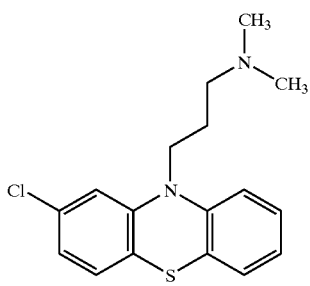

E-1

Chlorpromazine is currently available in the following forms: tablets, capsules, suppositories, oral concentrates and syrups, and formulations for injection.

Phenothiazines considered to be chlorpromazine analogs include fluphenazine, prochlorperazine, thioridazine, and trifluoperazine. Many of these share antipsychotic or antiemetic activity with chlorpromazine.

Phenothiazines are thought to elicit their antipsychotic and antiemetic effects via interference with central dopaminergic pathways in the mesolimbic and medullary chemoreceptor trigger zone areas of the brain. Extrapyramidal side effects are a result of interactions with dopaminergic pathways in the basal ganglia. Although often termed dopamine blockers, the exact mechanism of dopaminergic interference responsible for the drugs' antipsychotic activity has not been determined. Chlorpromazine has strong alpha-adrenergic blocking activity and can cause orthostatic hypotension. Chlorpromazine also has moderate anticholinergic activity manifested as occasional dry mouth, blurred vision, urinary retention, and constipation. Chlorpromazine increases prolactin secretion owing to its dopamine receptor blocking action in the pituitary and hypothalamus.

Chlorpromazine is readily absorbed from the gastrointestinal tract. Its bioavailability is variable due to considerable first pass metabolism by the liver. Liquid concentrates may have greater bioavailability than tablets. Food does not appear to affect bioavailability consistently. I.m. administration bypasses much of the first pass effect and higher plasma concentrations are achieved. The onset of action after i.m. administration is usually 15 to 30 minutes and after oral administration 30 to 60 minutes. Rectally administered chlorpromazine usually takes longer to act than orally administered chlorpromazine.

Chlorpromazine Metabolites

Because chlorpromazine undergoes extensive metabolic transformation into a number of metabolites that may be therapeutically active, these metabolites may be substituted from chlorpromazine in the antiproliferative combination of the invention. The metabolism of chlorpromazine yields, for example, oxidative N-demethylation to yield the corresponding primary and secondary amine, aromatic oxidation to yield a phenol, N-oxidation to yield the N-oxide, S-oxidation to yield the sulphoxide or sulphone, oxidative deamination of the aminopropyl side chain to yield the phenothiazine nuclei, and glucuronidation of the phenolic hydroxy groups and tertiary amino group to yield a quaternary ammonium glucuronide. In other examples of chlorpromazine metabolites useful in the antiproliferative combination of the invention, each of positions 3, 7, and 8 of the phenothiazine can independently be substituted with a hydroxyl or methoxyl moiety.

Pentamidine

Pentamidine is currently used for the treatment of *Pneumocystis carinii*, *Leishmania donovani*, *Trypanosoma brucei*, *T. gambiense*, and *T. rhodesiense* infections. The structure of pentamidine is:

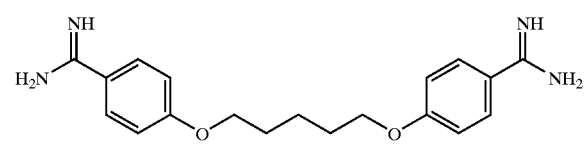
F-1

It is available formulated for injection or inhalation. For injection, pentamidine is packaged as a nonpyrogenic, lyophilized product. After reconstitution, it is administered by intramuscular or intravenous injection.

Pentamidine isethionate is a white, crystalline powder soluble in water and glycerin and insoluble in ether, acetone, and chloroform. It is chemically designated 4,4'-diamidinodiphenoxypentane di(β-hydroxyethanesulfonate). The molecular formula is $C_{23}H_{36}N_4O_{10}S_2$ and the molecular weight is 592.68.

The mode of action of pentamidine is not fully understood. In vitro studies with mammalian tissues and the protozoan *Crithidia oncopelti* indicate that the drug interferes with nuclear metabolism, producing inhibition of the synthesis of DNA, RNA, phospholipids, and proteins.

Little is also known about the drug's pharmacokinetics. In seven patients treated with daily i.m. doses of pentamidine at 4 mg/kg for 10 to 12 days, plasma concentrations were between 0.3 and 0.5 µg/mL. The patients continued to excrete decreasing amounts of pentamidine in urine up to six to eight weeks after cessation of the treatment.

Tissue distribution of pentamidine has been studied in mice given a single intraperitoneal injection of pentamidine at 10 mg/kg. The concentration in the kidneys was the highest, followed by that in the liver. In mice, pentamidine was excreted unchanged, primarily via the kidneys with some elimination in the feces. The ratio of amounts excreted in the urine and feces (4:1) was constant over the period of study.

Pentamidine Analogs

Aromatic diamidino compounds can replace pentamidine in the antiproliferative combination of the invention. Aromatic diamidino compounds such as propamidine, butamidine, heptamidine, and nonamidine share properties with pentamidine in that they exhibit antipathogenic or DNA binding properties. Other analogs (e.g., stilbamidine and indole analogs of stilbamidine, hydroxystilbamidine, diminazene, benzamidine, 4,4'-(pentamethylenedioxy) di-, dihydrochloride, phenamidine, dibrompropamidine, 1,3-bis(4-amidino-2-methoxyphenoxy)propane (DAMP), netropsin, distamycin, phenamidine, amicarbalide, bleomycin, actinomycin, and daunorubicin) also exhibit properties similar to those of pentamidine. It is likely that these compounds will have antiproliferative activity when administered in combination with chlorpromazine (or an analog or metabolite of chlorpromazine).

Preferred analogs are described, for example, by formula (II).

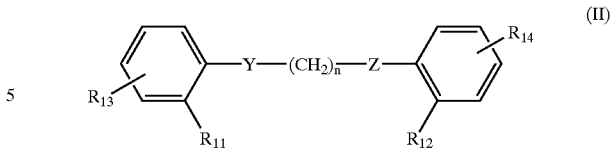
(II)

wherein each of Y and Z is, independently, O or N; each of $R_{11}$ and $R_{12}$ is, independently, H, OH, Cl, Br, $OCH_3$, $OCF_3$, $NO_2$, or $NH_2$; and n is an integer from 2 to 6, inclusive; and each of $R_{13}$ and $R_{14}$ is, independently, at the meta or para position and is selected from the group consisting of:

D-1

D-2

D-3

D-4

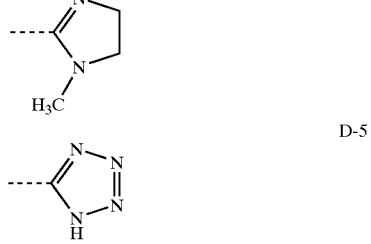
D-5

Other analogs include stilbamidine (G-1) and hydroxystilbamidine (G-2), and their indole analogs (e.g., G-3).

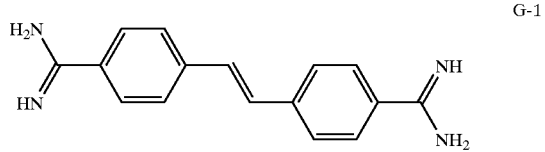
G-1

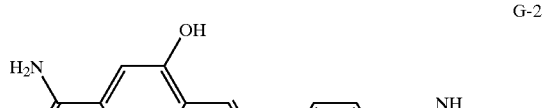
G-2

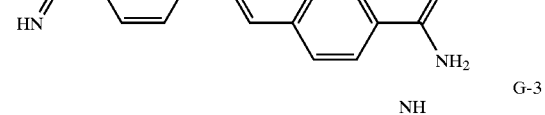
G-3

Each amidine moiety may be replaced with one of the moieties depicted as D-2, D-3, D-4, or D-5, above. As is the case for the phenothiazines and pentamidine, salts of stilbamidine and its related compounds are also useful in the method of the invention. Preferred salts include, for example, dihydrochloride and methanesulfonate salts.

Pentamidine Metabolites

Pentamidine metabolites are also useful in the antiproliferative combination of the invention. Pentamidine is rapidly metabolized in the body to at least seven primary metabolites. Some of these metabolites share one or more activities with pentamidine. It is likely that some pentamidine metabolites will exhibit antiproliferative activity when combined with chlorpromazine or an analog thereof.

Seven pentamidine metabolites are shown below.

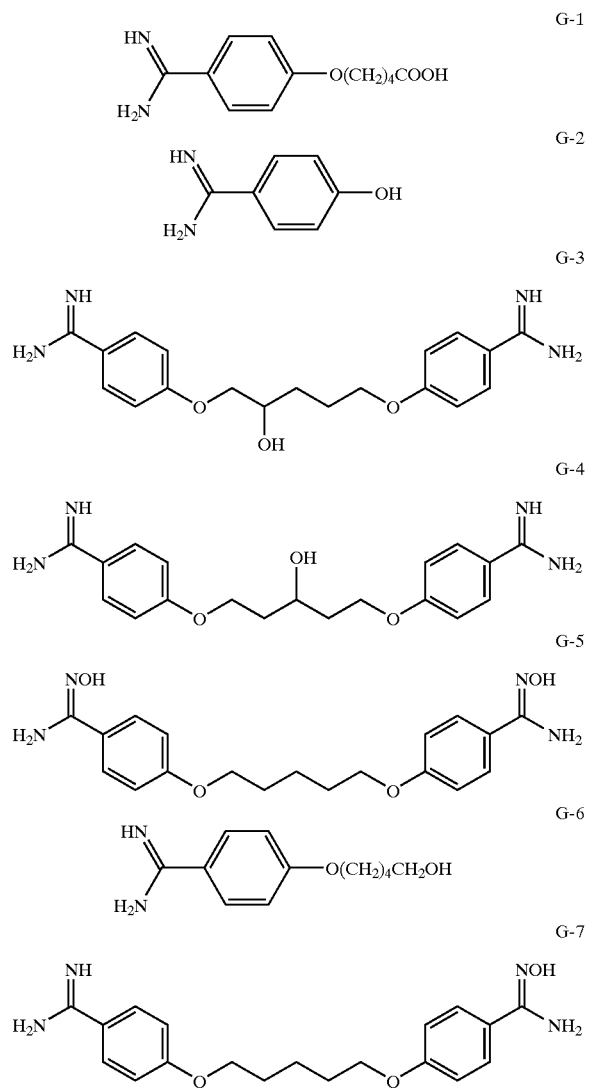

Therapy

The combinations of compounds of the invention are useful for the treatment of neoplasms. Combination therapy may be performed alone or in conjunction with another therapy (e.g., surgery, radiation, chemotherapy, biologic therapy). Additionally, a person having a greater risk of developing a neoplasm (e.g., one who is genetically predisposed or one who previously had a neoplasm) may receive prophylactic treatment to inhibit or delay neoplastic formation.

The administration dosage and frequency of each component can be controlled independently. For example, one compound may be administered orally three times per day, while the second compound may be administered intramuscularly once per day. The compounds may also be formulated together such that one administration delivers both components. Formulations and dosages are described below.

Formulation of Pharmaceutical Compositions

The administration of each compound of the combination may be by any suitable means that results in a concentration of the compound that, combined with the other component, is specifically anti-neoplastic upon reaching the target region. The compound may be contained in any appropriate amount in any suitable carrier substance, and is generally present in an amount of 1–95% by weight of the total weight of the composition. The composition may be provided in a dosage form that is suitable for the oral, parenteral (e.g., intravenously, intramuscularly), rectal, cutaneous, nasal, vaginal, inhalent, skin (patch), or ocular administration route. Thus, the composition may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols. The pharmaceutical compositions may be formulated according to conventional pharmaceutical practice (see, e.g., *Remington: The Science and Practice of Pharmacy*, (19th ed.) ed. A. R. Gennaro, 1995, Mack Publishing Company, Easton, Pa. and *Encyclopedia of Pharmaceutical Technology*, eds. J. Swarbrick and J. C. Boylan, 1988–1999, Marcel Dekker, New York.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance (sawtooth kinetic pattern); (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of compounds in the form of a controlled release formulation is especially preferred in cases in which the compound, either alone or in combination, has (i) a narrow therapeutic index (i.e., the difference between the plasma concentration leading to harmful side effects or toxic reactions and the plasma concentration leading to a therapeutic effect is small; in general, the therapeutive index, TI, is defined as the ratio of median lethal dose ($LD_{50}$) to median effective dose ($ED_{50}$)); (ii) a narrow absorption window in the gastro-intestinal tract; or (iii) a very short biological half-life so that frequent dosing during a day is required in order to sustain the plasma level at a therapeutic level.

Any of a number of strategies can be applied in order to obtain a controlled release formulation in which the rate of release outweighs the rate of metabolism of the compound in question. In one example, controlled release is obtained by appropriate selection of various formulation parameters and ingredients, including, e.g., various types of controlled release compositions and coatings. Thus, the drug substance is formulated with appropriate excipients into a pharmaceutical composition that, upon administration to the organism, releases the active substance in a controlled manner. Examples include single or multiple unit tablet or capsule compositions, oil solutions, suspensions, emulsions, microcapsules, microspheres, nanoparticles, patches, and liposomes.

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in *Encyclopedia of Pharmaceutical Technology*, supra.

The two drugs may be mixed together in the tablet, or may be partitioned. In one example, the first drug is contained on the inside of the tablet, and the second drug is on the outside, such that a substantial portion of the second drug is released prior to the release of the first drug.

Formulations for oral use may also be presented as chewing tablets, or as hard gelatin capsules wherein the active ingredient is mixed with an inert solid diluent (e.g., potato starch, lactose, microcrystalline cellulose, calcium carbonate, calcium phosphate or kaolin, or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active drug substance by controlling the dissolution and/or the diffusion of the active drug substance.

Dissolution or diffusion controlled release can be achieved by appropriate coating of a tablet, capsule, pellet, or granulate formulation of compounds, or by incorporating the compound in question into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the compounds of the claimed combinations may also be in the form of a buoyant tablet or capsule (i.e., a tablet or capsule that, upon oral administration, floats on top of the gastric content for a certain period of time. A buoyant tablet formulation of the compound(s) can be prepared by granulating a mixture of the drug(s) with excipients and 20–75% w/w of hydrocolloids, such as hydroxyethrlcellulose, hydroxypropylcellulose and hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions is well-known to those skilled in the art of pharmaceutical formulation. Specific formulations can be found in *Remington: The Science and Practice of Pharmacy*, supra.

Compositions for parenteral use may be presented in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10–60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices.

Materials for use in the preparation of microspheres and/or microcapsules are, e.g., biodegradable/bioerodible polymers such as polyglactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies.

Materials for use in implants can be non-biodegradable (e.g., polydimethyl siloxane) or biodegradable (e.g., poly (caprolactone), poly(lactic acid), poly(glycolic acid) or poly (ortho esters)).

Rectal Compositions

For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives, enhancers, or surfactants may be incorporated.

Compositions for Inhalation

For administration by inhalation, typical dosage forms include nasal sprays and aerosols. In a typically nasal formulation, the active ingredient(s) are dissolved or dispersed in a suitable vehicle. The pharmaceutically acceptable vehicles and excipients (as well as other pharmaceutically acceptable materials present in the composition such as diluents, enhancers, flavoring agents, and preservatives) are selected in accordance with conventional pharmaceutical practice in a manner understood by the persons skilled in the art of formulating pharmaceuticals.

Percutaneous and Topical Compositions

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gelforming agents, ointment bases, perfumes, and skin protective agents.

Examples of emulsifying agents are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and Azone™. Examples of chelating agents are sodium EDTA, citric acid, and phosphoric acid. Examples of gel forming agents are Carbopol™, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (Tween)).

The pharmaceutical compositions described above for topical administration on the skin may also be used in connection with topical administration onto or close to the part of the body that is to be treated. The compositions may be adapted for direct application or for introduction into relevant orifice(s) of the body (e.g., rectal, urethral, vaginal or oral orifices). The composition may be applied by means of special drug delivery devices such as dressings or alternatively plasters, pads, sponges, strips, or other forms of suitable flexible material.

Controlled Release Percutaneous and Topical Compositions

There are several approaches for providing rate control over the release and transdermal permeation of a drug, including: membrane-moderated systems, adhesive diffusion-controlled systems, matrix dispersion-type systems, and microreservoir systems. A controlled release percutaneous and/or topical composition may be obtained by using a suitable mixture of the above-mentioned approaches.

In a membrane-moderated system, the active drug is present in a reservoir which is totally encapsulated in a shallow compartment molded from a drug-impermeable laminate, such as a metallic plastic laminate, and a rate-controlling polymeric membrane such as a microporous or a non-porous polymeric membrane (e.g., ethylene-vinyl acetate copolymer). The active compound is only permitted to be released through the rate-controlling polymeric membrane. In the drug reservoir, the active drug substance may either be dispersed in a solid polymer matrix or suspended in a viscous liquid medium such as silicone fluid. On the external surface of the polymeric membrane, a thin layer of an adhesive polymer is applied to achieve an intimate contact of the transdermal system with the skin surface. The adhesive polymer is preferably a hypoallergenic polymer that is compatible with the active drug.

In an adhesive diffusion-controlled system, a reservoir of the active drug is formed by directly dispersing the active drug in an adhesive polymer and then spreading the adhesive containing the active drug onto a flat sheet of substantially drug-impermeable metallic plastic backing to form a thin drug reservoir layer. A matrix dispersion-type system is characterized in that a reservoir of the active drug substance is formed by substantially homogeneously dispersing the active drug substance in a hydrophilic or lipophilic polymer matrix and then molding the drug-containing polymer into a disc with a substantially well-defined surface area and thickness. The adhesive polymer is spread along the circumference to form a strip of adhesive around the disc.

In a microreservoir system, the reservoir of the active substance is formed by first suspending the drug solids in an aqueous solution of water-soluble polymer, and then dispersing the drug suspension in a lipophilic polymer to form a plurality of microscopic spheres of drug reservoirs.

Dosages

The dosage of each compound of the claimed combination depends on several factors, including: the administration method, the disease to be treated, the severity of the disease, whether the disease is to be treated or prevented, and the age, weight, and health of the person to be treated.

The compounds are preferably administered in an amount of about 0.1–30 mg/kg body weight per day, and more preferably in an amount of about 0.5–15 mg/kg body weight per day. As described above, the compound in question may be administered orally in the form of tablets, capsules, elixirs or syrups, or rectally in the form of suppositories. Parenteral administration of a compound is suitably performed in the form of saline solutions or with the compound incorporated into liposomes. In cases where the compound in itself is not sufficiently soluble to be dissolved, a solubilizer such as ethanol can be applied. Below, for illustrative purposes, the dosages for chlorpromazine and pentamidine are described. One in the art will recognize that if a second compound is substituted for either chlorpromazine or pentamidine, the correct dosage can be determined by examining the efficacy of the compound in cell proliferation assays, as well as its toxicity in humans.

Oral Administration

For chlorpromazine adapted for oral administration for systemic use, the dosage is normally about 1 mg to 1000 mg per dose administered (preferably about 5 mg to 500 mg, and more preferably about 10 mg to 300 mg) one to ten times daily (preferably one to 5 times daily) for one day to one year, and may even be for the life of the patient; because the combinations of the invention function primarily as cytostatic rather than cytotoxic agents, and exhibit low toxicity, chronic, long-term administration will be indicated in many cases. Dosages up to 8 g per day may be necessary.

For pentamidine, the dosage is normally about 0.1 mg to 300 mg per dose administered (preferably about 1 mg to 100 mg) one to four times daily for one day to one year, and, like chlorpromazine, may be administered for the life of the patient. Administration may also be given in cycles, such that there are periods during which time pentamidine is not administered. This period could be, for example, about a day, a week, a month, or a year or more.

Rectal Administration

For compositions adapted for rectal use for preventing disease, a somewhat higher amount of a compound is usually preferred. Thus a dosage of chlorpromazine is normally about 5 mg to 2000 mg per dose (preferably about 10 mg to 1000 mg, more preferably about 25 mg to 500 mg) administered one to four times daily. Treatment lengths are as described for oral administration. The dosage of pentamidine is as described for orally administered pentamidine.

Parenteral Administration

For intravenous or intramuscular administration of chlorpromazine, a dose of about 0.1 mg/kg to about 100 mg/kg body weight per day is recommended, a dose of about 1 mg/kg to about 25 mg/kg is preferred, and a dose of 1 mg/kg to 10 mg/kg is most preferred. Pentamidine is administered at a dose of about 0.1 mg/kg to about 20 mg/kg, preferably at a dose of about 0.5 mg/kg to about 10 mg/kg, and more preferably at a dose of about 1 mg/kg to about 4 mg/kg.

Each compound is usually administered daily for up to about 6 to 12 months or more. It may be desirable to administer a compound over a one to three hour period; this period may be extended to last 24 hours or more. As is described for oral administration, there may be periods of about one day to one year or longer during which at least one of the drugs is not administered.

Inhalation

For inhalation, chlorpromazine is administered at a dose of about 1 mg to 1000 mg daily, and preferably at a dose of about 10 mg to 500 mg daily. For pentamidine, a dose of about 10 mg to 1000 mg, and preferably at a dose of 30 mg to 600 mg, is administered daily.

Percutaneous Administration

For topical administration of either compound, a dose of about 1 mg to about 5 g administered one to ten times daily for one week to 12 months is usually preferable.

The following examples are to illustrate the invention. They are not meant to limit the invention in any way.

EXAMPLE 1

Preparation of the Chlorpromazine/Pentamidine Isethionate Dilution Matrix

Stock solutions of chlorpromazine and pentamidine isethionate (Sigma catalog number C8138 and P0547, respectively) were made in dimethylsulfoxide (DMSO) at concentrations of 11.25 mM and 6.74 mM respectively. An 8× stock solution (128 $\mu$M) of each individual compound was made in Dulbecco's Modified Eagle Medium (DMEM) (Gibco 11995–040) containing 10% fetal bovine serum (FBS), 200 mM L-glutamine, and 1% antibiotic/antimycotic solution. From this a 2-fold dilution series was made in DMEM. This series provided 9 concentrations ranging from 64 $\mu$M to 240 nM and one concentration of 0 M. The compound mixture matrix was prepared by filling columns of a 384-well plate with the dilution series of chlorpromazine (first column: 32 $\mu$M; second column: 16 $\mu$M; third column: 8 $\mu$M; fourth column: 4 $\mu$M; fifth column: 2 $\mu$M; sixth column: 1 $\mu$M; seventh column: 500 nM; eighth column: 250 nM; ninth column: 125 nM; and tenth column: no compound) and filling the rows with the dilution series of pentamidine (first column: 32 μM; second column: 16 μM; third column: 8 μM; fourth column: 4 μM; fifth column: 2 μM; sixth column: 1 μM; seventh column: 500 nM; eighth column: 250 nM; ninth column: 125 nM; and tenth column: no compound) using a 16-channel pipettor (Finnpipette). This compound mixture plate provided 4× concentrations of each compound that are transferred to assay plates. The dilution matrix thus contained 100 different points—81 wells where varying amounts of chlorpromazine and pentamidine were present, as well as a 10 point dilution series (2-fold) for each individual compound.

EXAMPLE 2

Assay for Antiproliferative Activity

The compound dilution matrix was assayed using the A549 bromodeoxyuridine (BrdU) cytoblot method. Forty-five microliters of a suspension containing A549 lung adenocarcinoma cells (ATCC# CCL-185) was seeded in a white opaque polystyrene cell culture treated sterile 384-well plate (NalgeNunc #164610) using a multidrop (Labsystems) to give a density of 3000 cells per well. Fifteen microliters of the 4× compound mixture matrix was added to each well of the plate containing the cells. The compound mixture matrix was transferred using a 16-channel pipettor (Finnpipette). In addition, control wells with paclitaxel (final concentration 4.6 μM), podophyllotoxin (9.6 μM), and quinacrine (8.5 μM) were added to each plate. Each experiment was conducted in triplicate plates.

After incubation for 48 hours at 37° C., BrdU was added to each well at a concentration of 10 μM. After 16 hours, the media was aspirated and the cells were fixed by the addition of 70% ethanol and phosphate-buffered saline (PBS) at room temperature for 1 hour. The fixative was aspirated and 2N HCl with Tween 20 (polyoxyethylene sorbitan monolaurate) was added to each well and the plates were incubated for 20 minutes at room temperature. The HCl was neutralized with a solution of 2N NaOH and the cells were washed twice with Hank's Balanced Salt Solution (HBSS) and once with PBS containing 0.5% bovine serum albumin (BSA) and 0.1% Tween 20. The wash solution was removed and mouse anti-BrdU primary antibody (PharMingen #555627) was diluted 1:1000 in PBS containing BSA, Tween 20, and secondary antibody at a dilution of 1:2000 (Amersham #NA931). The secondary antibody recognizes the mouse antibody and it is conjugated to the enzyme horseradish peroxidase (HRP). After one hour of incubation, the antibody solution was removed and the cells washed once with PBS. After the PBS wash, the HRP substrate (which contains luminol, hydrogen peroxide, and an enhancer such as para-iodophenol) was added to each well. The plates were read using an LJL Analyst. All aspirations as well as the washes with PBS and HBSS were performed using a TECAN Power Washer 384. The amount of light output from each well indicates the amount of DNA synthesis that occurred in that well. Decreased light indicates antiproliferative action of the compounds.

Luminescence for each position in the chlorpromazine/pentamidine dilution matrix was divided into the luminescence values for A549 cells treated with only DMSO vehicle, providing antiproliferative ratios for each position in the chlorpromazine/pentamidine dilution matrix. Antiproliferative ratios were also calculated for paclitaxel, podophyllotoxin and quinacrine and used for comparison.

TABLE

| Chlorpromazine Concentrations (μM) | Antiproliferative Ratios |||||||||| 
| | Pentamidine Concentrations (μM) |||||||||| 
| | 8 | 4 | 2 | 1 | 0.5 | 0.25 | 0.13 | 0.06 | 0.03 | 0 |
|---|---|---|---|---|---|---|---|---|---|---|
| 8 | 6.8 | 6.3 | 5.1 | 3.7 | 2.7 | 3.1 | 2.4 | 2.3 | 2.3 | 2.6 |
| 4 | 7.8 | 9.7 | 5.9 | 5.5 | 4.0 | 4.3 | 4.1 | 3.2 | 2.8 | 2.9 |
| 2 | 8.4 | 9.0 | 4.8 | 4.5 | 5.0 | 3.6 | 3.2 | 3.0 | 2.3 | 2.4 |
| 1 | 8.0 | 6.9 | 5.1 | 5.6 | 4.7 | 3.3 | 2.8 | 2.3 | 1.9 | 1.8 |
| 0.5 | 7.6 | 7.0 | 4.4 | 4.9 | 2.9 | 3.3 | 1.9 | 1.8 | 1.6 | 1.7 |
| 0.25 | 6.6 | 6.1 | 3.7 | 6.2 | 3.7 | 3.8 | 1.6 | 1.6 | 1.3 | 1.3 |
| 0.13 | 6.2 | 4.7 | 3.0 | 5.2 | 2.8 | 2.4 | 1.4 | 1.3 | 1.1 | 1.2 |
| 0.06 | 5.0 | 5.0 | 3.1 | 3.0 | 2.3 | 2.0 | 1.3 | 1.1 | 1.2 | 1.0 |
| 0.03 | 4.3 | 4.1 | 3.2 | 3.0 | 2.6 | 1.9 | 1.2 | 1.1 | 1.0 | 1.1 |
| 0 | 4.9 | 3.9 | 3.0 | 2.9 | 3.0 | 2.3 | 1.4 | 1.2 | 0.9 | 1.0 |

At 4.0 μM, pentamidine isethionate alone yields an antiproliferative ratio of 3.9 and this increases to 4.9 when the concentration is doubled to 8.0 μM. Four micromolar chlorpromazine yields a ratio of 2.9, and this is increased no further by doubling the concentration to 8.0 μM. When 4.0 μM pentamidine is tested in combination with 4.0 μM chlorpromazine (8.0 μM total compound species), an antiproliferative ratio of 9.7 is achieved.

In another analysis, the potency of the single compounds is shifted by the presence of the other compound. The maximal antiproliferative ratio achieved by pentamidine alone was 4.9 (at 8.0 μM) and this was observed when 1 μM pentamidine was combined with chlorpromazine at concentrations as low as 125 nM, significantly reducing the total drug species needed to achieve this effect.

We demonstrated that the combination of chlorpromazine and pentamidine isethionate arrests the growth of A549 cells without killing them. A549 cells were seeded at subconfluence in 6-well plates and treated with 4 μM of each drug for 72 hours. The medium was exchanged and the cells cultured for seven days (with one medium change), at which time the cells were counted and viability determined. Whereas untreated cells had grown to confluence after seven days, the cells treated with chlorpromazine/pentamidine isethionate had not grown, but had remained near the density at which they were seeded. Additionally, 95% of chlorpromazine/pentamidine isethionate-treated cells were still viable, only slightly less than that observed for the untreated cells.

The combinations have little or no effect on the viability of normal lung fibroblasts (MRC9). The control experiments demonstrating this are described below. MRC9 cells were seeded into 384 well plates to confluence. A chlorpromazine/pentamidine isethionate dilution matrix was added to give overlapping 2-fold dilution series in a 12×12 matrix, with 16 μM of each compound being the maximal dose. The cells were incubated with the compounds for 48 hours, after which time 6 μL of Alamar Blue viability dye was added to each well. The cells were incubated an additional 4 hours with the dye. The amount of reduced dye was then determined by fluorescence using an Analyst AD. The nonfluorescent (oxidized) form of the dye is reduced to a fluorescent form by living cells. Thus, the ratio of fluorescence between the wells that did not receive compounds over those that did receive compounds is proportional to the amount of cell death caused by the compounds. In this experiment, no toxic effects were present until each drug reached a concentration of 16 μM, whereas the antiproliferative effects were observed at lower concentrations.

The anti-proliferative effect demonstrated with A459 cells can be similarly demonstrated using other cancer cell lines, such as MCF7 mammary adenocarcinoma, PA-1 ovarian teratocarcinoma, HT29 colorectal adenocarcinoma, H1299 large cell carcinoma, U-2 OS osteogenic sarcoma, U-373 MG glioblastoma, Hep-3B hepatocellular carcinoma, BT-549 mammary carcinoma, T-24 bladder cancer, C-33A cervical carcinoma, HT-3 metastatic cervical carcinoma, SiHa squamous cervical carcinoma, CaSki epidermoid cervical carcinoma, NCI-H292 mucoepidermoid lung carcinoma, NCI-2030, non small cell lung carcinoma, HeLa, epithelial cervical adenocarcinoma, KB epithelial mouth carcinoma, HT1080 epithelial fibrosarcoma, Saos-2 epithelial osteogenic sarcoma, PC3 epithelial prostate adenocarcinoma, SW480 colorectal carcinoma, CCL-228, and MS-751 epidermoid cervical carcinoma cell lines. The specificity can be tested by using cells such as NHLF lung fibroblasts, NHDF dermal fibroblasts, HMEC mammary epithelial cells, PrEC prostate epithelial cells, HRE renal epithelial cells, NHBE bronchial epithelial cells, CoSmC Colon smooth muscle cells, CoEC colon endothelial cells, NHEK epidermal keratinocytes, and bone marrow cells as control cells.

Other Embodiments

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology or related fields are intended to be within the scope of the invention.

What is claimed is:

1. A method for treating a patient having cancer, said method comprising administering to said patient:

a) a first compound having the formula (I):

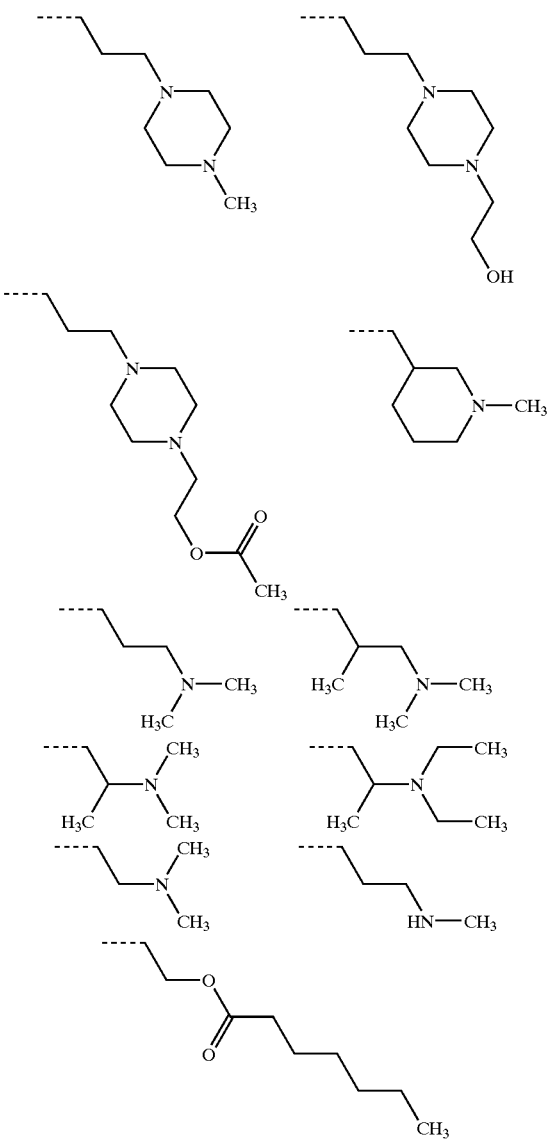

or a pharmaceutically acceptable salt thereof, wherein $R_2$ is selected from the group consisting of:

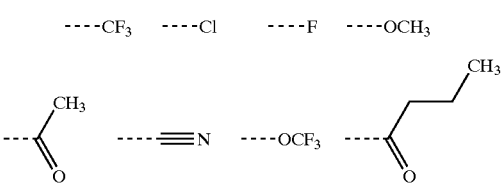

$R_{10}$ is selected from the group consisting of:

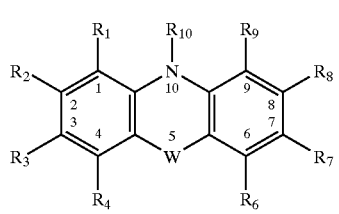

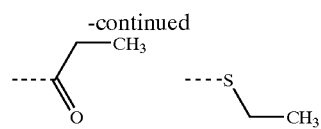

each of $R_1$, $R_3$, $R_4$, $R_5$, $R_6$, $R_7$, $R_8$, and $R_9$ is, independently, H, OH, F, $OCF_3$, or $OCH_3$; and W is selected from the group consisting of:

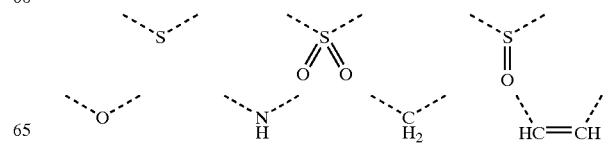

and b) a second compound having the formula (II):

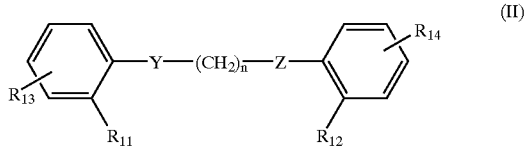

or a pharmaceutically acceptable salt thereof, wherein each of Y and Z is, independently, O or N; each of $R_{11}$ and $R_{12}$ is, independently, H, Cl, Br, OH, $OCH_3$, $OCF_3$, $NO_2$, and $NH_2$; n is an integer between 2 and 6, inclusive; and each of $R_{13}$ and $R_{14}$ is, independently, selected from the group consisting of:

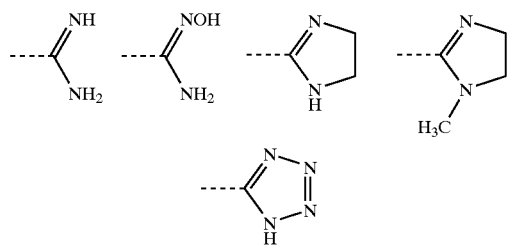

wherein said first and second compounds are administered simultaneously or within 14 days of each other in amounts sufficient to treat said patient.

2. The method of claim 1, wherein said first and second compounds are administered within ten days of each other.

3. The method of claim 2, wherein said first and second compounds are administered within five days of each other.

4. The method of claim 3, wherein said first and second compounds are administered within twenty-four hours of each other.

5. The method of claim 1, said method further comprising administering to said patient one or more a chemotherapeutic agents selected from paclitaxel, docetaxel, tamoxifen, vinorelbine, gemcitabine, cisplatin, etoposide, topotecan, irinotecan, anastrozole, rituximab, trastuzumab, fludarabine, cyclophosphamide, gentuzumab, carboplatin, interferon, 5-FU, doxorubicin, and cytoxan.

6. The method of claim 5, wherein said first and second compounds are administered within ten days of each other.

7. The method of claim 6, wherein said first and second compounds are administered within five days of each other.

8. The method of claim 7, wherein said first and second compounds are administered within twenty-four hours of each other.

9. The method of claim 1, wherein said cancer is brain cancer, breast cancer, cervical cancer, colon cancer, gastric cancer, kidney cancer, leukemia, liver cancer, lung cancer, lymphoma, ovarian cancer, pancreatic cancer, prostate cancer, rectal cancer, sarcoma, skin cancer, testicular cancer, or uterine cancer.

10. The method of claim 9, wherein said first and second compounds are administered within ten days of each other.

11. The method of claim 10, wherein said first and second compounds are administered within five days of each other.

12. The method of claim 11, wherein said first and second compounds are administered within twenty-four hours of each other.

13. A method for treating a patient having brain cancer, breast cancer, cervical cancer, colon cancer, gastric cancer, kidney cancer, leukemia, liver cancer, lung cancer, lymphoma, ovarian cancer, pancreatic cancer, prostate cancer, rectal cancer, sarcoma, skin cancer, testicular cancer, or uterine cancer, said method comprising administering to said patient:

a) a first compound having the formula (I):

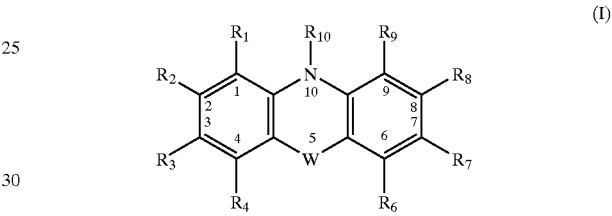

or a pharmaceutically acceptable salt thereof, wherein $R_2$ is selected from the group consisting of:

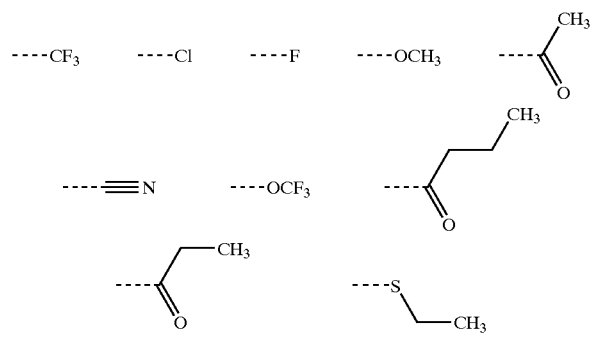

$R_{10}$ is selected from the group consisting of:

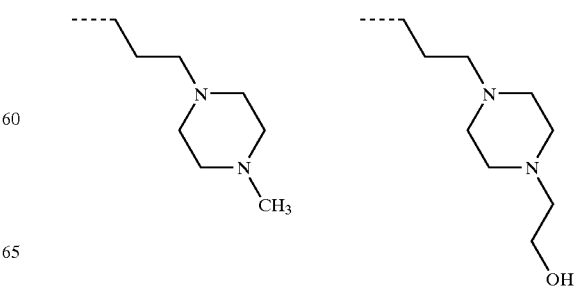

-continued

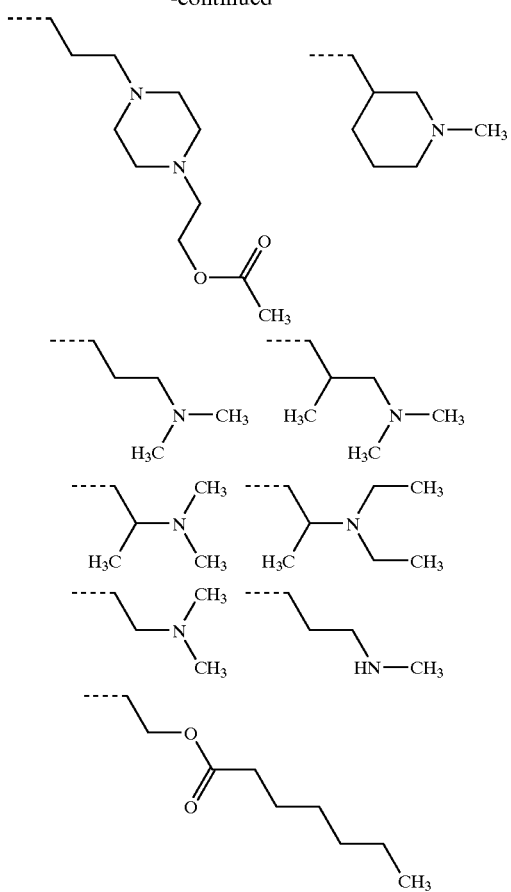

each of $R_1$, $R_3$, $R_4$, $R_5$, $R_6$, $R_7$, $R_8$, and $R_9$ is, independently, H, OH, F, $OCF_3$, or $OCH_3$; and W is selected from the group consisting of:

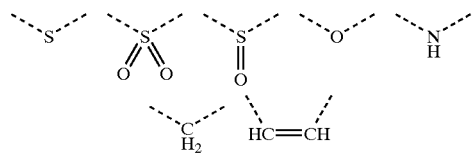

and b) a second compound having the formula (II):

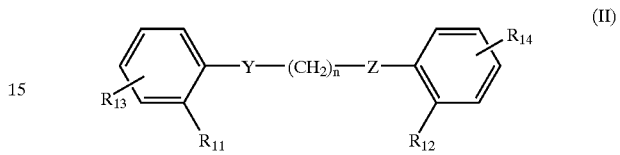

(II)

or a pharmaceutically acceptable salt thereof, wherein each of Y and Z is, independently, O or N; each of $R_{11}$ and $R_{12}$ is, independently, H, Cl, Br, OH, $OCH_3$, $OCF_3$, $NO_2$, and $NH_2$; n is an integer between 2 and 6, inclusive; and each of $R_{13}$ and $R_{14}$ is, independently, selected from the group consisting of:

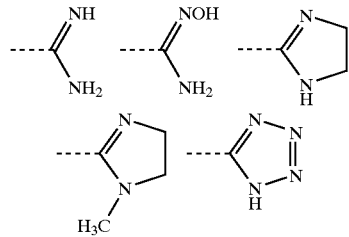

wherein said first and second compounds are administered simultaneously or within 24 hours of each other in amounts sufficient to treat said patient.

* * * * *

UNITED STATES PATENT AND TRADEMARK OFFICE
CERTIFICATE OF CORRECTION

PATENT NO. : 6,846,816 B2
APPLICATION NO. : 10/347714
DATED : January 25, 2005
INVENTOR(S) : Borisy et al.

It is certified that error appears in the above-identified patent and that said Letters Patent is hereby corrected as shown below:

On the Title page item (56), in References Cited, in OTHER PUBLICATIONS,
 line 1, Bornstein et al., replace "Evalution" with --Evaluation--;
 Page 2, Col. 1, line 45, Ganapathi et al., replace "Goverming" with --Governing--;
 Page 2, Col. 1, line 57, Huilgol et al., replace "*Joumal*" with --*Journal*--;
 Page 2, Col. 2, line 8, Jansen et al., replace "et al," with --et al.,--;
 Page 2, Col. 2, line 39, Libby et al., replace "Parmacology" with --Pharmacology--;.
 Page 2, Col. 2, line 46, Mesa-Valle et al. (1989), replace "ValIe" with --Valle--; and
 Page 2, Col. 2, line 52, Mesa-Valle CM et al., replace "ValIe" with --Valle--.

Column 2,
 Line 17, replace "putaperazine" with --butaperazine--.

Column 16,
 Line 29, replace "metylcellulose" with --methylcellulose--; and
 Line 40, replace "hydroxyethrlcellulose" with --hydroxyethylcellulose--.

Column 25,
 Line 55, replace "one or more a" with --one or more--.

Signed and Sealed this

Seventeenth Day of April, 2007

JON W. DUDAS
*Director of the United States Patent and Trademark Office*